(12) United States Patent
Park et al.

(10) Patent No.: US 10,782,283 B2
(45) Date of Patent: Sep. 22, 2020

(54) ELECTRONIC DEVICE AND METHOD OF CALCULATING FORMATION TIME OF PERIMETER STAIN

(71) Applicant: Republic of Korea (National Forensic Service Director Ministry of Public Administration and Security), Seoul (KR)

(72) Inventors: Nam Kyu Park, Bucheon-si (KR); Jae Mo Goh, Wonju-si (KR); Jin Pyo Kim, Yuseong-gu (KR); Young Il Seo, Wonju-si (KR); Eun Ah Joo, Yongin-si (KR); Je Hyun Lee, Wonju-si (KR); Sang Yoon Lee, Siheung-si (KR); Dong A Lim, Yuseong-gu (KR); Ki Hwan Kim, Yongin-si (KR)

(73) Assignee: Republic of Korea (National Forensic Service Director Ministry of Public Administration and Security), Seoul (KR)

( * ) Notice: Subject to any disclaimer, the term of this patent is extended or adjusted under 35 U.S.C. 154(b) by 71 days.

(21) Appl. No.: 16/175,646

(22) Filed: Oct. 30, 2018

(65) Prior Publication Data

US 2019/0369082 A1 Dec. 5, 2019

(30) Foreign Application Priority Data

May 29, 2018 (KR) ........................ 10-2018-0061283

(51) Int. Cl.
*G06K 9/00* (2006.01)
*G01N 33/49* (2006.01)
(Continued)

(52) U.S. Cl.
CPC .............. *G01N 33/49* (2013.01); *G01B 11/02* (2013.01); *G06T 7/60* (2013.01);
(Continued)

(58) Field of Classification Search
CPC .... H04N 5/232935; G01B 11/02; G06T 7/60; G06T 7/194; G06T 2207/20092; G06T 2207/30004
(Continued)

(56) References Cited

U.S. PATENT DOCUMENTS 6,692,967 B1 * 2/2004 Di Benedetto .... G01N 21/6447
356/39
2013/0137127 A1 * 5/2013 Berezin .............. G01N 21/6486
435/25

(Continued)

FOREIGN PATENT DOCUMENTS

KR 20150133500 11/2015
KR 101588323 1/2016
(Continued)

OTHER PUBLICATIONS

"Korean Application Serial No. 10-2018-0061283, Notice of Allowance dated Feb. 22, 2019", w/o English Translation, 8 pgs.
(Continued)

*Primary Examiner* — Gabriel I Garcia
(74) *Attorney, Agent, or Firm* — Schwegman Lundberg & Woessner, P.A.

(57) ABSTRACT

According to the present disclosure, a method of calculating a formation time of a perimeter stain is performed by a device for calculating a formation time of a perimeter stain, and includes obtaining a captured image of an analysis target by using a camera, extracting an image of a perimeter stain included in the analysis target, by analyzing the obtained captured image, calculating a major axis length and a width of the perimeter stain, estimating a formation time of the perimeter stain by using the major axis length and the width of the perimeter stain, and outputting the image of the perimeter stain and the formation time of the perimeter stain.

21 Claims, 9 Drawing Sheets

(51) Int. Cl.
  *G01B 11/02* (2006.01)
  *G06T 7/60* (2017.01)
  *H04N 5/232* (2006.01)
  *G06T 7/194* (2017.01)

(52) U.S. Cl.
  CPC ....... *H04N 5/232935* (2018.08); *G06T 7/194* (2017.01); *G06T 2207/20092* (2013.01); *G06T 2207/30004* (2013.01)

(58) Field of Classification Search
  USPC ........................................................ 382/128
  See application file for complete search history.

(56) References Cited

U.S. PATENT DOCUMENTS

| | | | | |
|---|---|---|---|---|
| 2013/0196443 | A1* | 8/2013 | Aalders | G01J 3/0218 436/66 |
| 2015/0348261 | A1* | 12/2015 | Sunami | A61B 6/032 382/131 |
| 2016/0225179 | A1* | 8/2016 | Sheppard | G06F 40/134 |
| 2017/0150904 | A1 | 6/2017 | Park et al. | |
| 2019/0285550 | A1* | 9/2019 | Lednev | G01J 3/44 |
| 2019/0328317 | A1* | 10/2019 | Mochizuki | A61B 5/489 |
| 2019/0370991 | A1* | 12/2019 | Park | G06T 7/60 |

FOREIGN PATENT DOCUMENTS

| | | |
|---|---|---|
| KR | 101588322 | 2/2016 |
| KR | 10-182089 B1 | 12/2017 |
| KR | 101812089 | 12/2017 |
| KR | 20180007390 | 1/2018 |

OTHER PUBLICATIONS

Korean Application No. 10-2018-0061283, Office Action dated Oct. 15, 2018, 6 pgs.

Kim, K., et al., "Study on the determination of creation time of skeletonization stain", Korean Journal of Forensic Sciences, 18, with English abstract, (2017), 48-52.

Ramsthaler, F., et al., "Drying properties of bloodstains on common indoor surfaces", Int. J. Legal Med., 126, (2012), 739-746.

* cited by examiner

ELECTRONIC DEVICE AND METHOD OF CALCULATING FORMATION TIME OF PERIMETER STAIN

CROSS-REFERENCE TO RELATED APPLICATION

This application claims the benefit of Korean Patent Application No. 10-2018-0061283, filed on May 29, 2018, in the Korean Intellectual Property Office, the disclosure of which is incorporated herein in its entirety by reference.

BACKGROUND

1. Field

One or more embodiments relate to an electronic device and a method of calculating a formation time of a perimeter stain.

2. Description of the Related Art

A formation time of a perimeter stain formed when a drip stain is wiped may serve as a critical clue to solving a bloody crime. However, up to now, there isn't a device capable of calculating a formation time of a perimeter stain. Therefore, a program capable of easily calculating a formation time of a perimeter stain on the spot is necessary.

SUMMARY

One or more embodiments include an electronic device for calculating a formation time of a perimeter stain, a method of calculating a formation time of a perimeter stain, and a computer program recorded on a recording medium to execute the method.

Additional aspects will be set forth in part in the description which follows and, in part, will be apparent from the description, or may be learned by practice of the presented embodiments.

According to one or more embodiments, a method of calculating a formation time of a perimeter stain is performed by a device for calculating a formation time of a perimeter stain, and includes obtaining a captured image of an analysis target by using a camera, extracting an image of a perimeter stain included in the analysis target, by analyzing the obtained captured image, calculating a major axis length and a width of the perimeter stain, estimating a formation time of the perimeter stain by using the major axis length and the width of the perimeter stain, and outputting the image of the perimeter stain and the formation time of the perimeter stain.

The calculating of the major axis length and the width of the perimeter stain may include generating a first guide line corresponding to a major axis of the perimeter stain, generating a second guide line corresponding to the width of the perimeter stain, and calculating the major axis length of the perimeter stain by using the first guide line, and calculating the width of the perimeter stain by using the second guide line.

The first guide line or the second guide line may be output through an output unit, and may be adjusted in location, size, or shape based on a user input.

The estimating of the formation time of the perimeter stain may include calculating the formation time of the perimeter stain by substituting the major axis length and the width of the perimeter stain in a pre-registered equation.

The device for calculating a formation time of a perimeter stain may include a first button used to obtain the captured image, and a second button used to calculate the formation time of the perimeter stain.

The obtaining of the captured image of the analysis target may include obtaining a captured image from an external imaging device.

The method may further include transmitting the captured image and the formation time of the perimeter stain to an external device, after the formation time of the perimeter stain is estimated.

According to one or more embodiments, an electronic device includes a camera, an input unit, an output unit, a processor, and a storage medium having stored therein instructions executable by the processor, wherein the processor executes the instructions and includes an image obtainer configured to obtain a captured image of an analysis target by using the camera, a bloodstain image extractor configured to extract an image of a perimeter stain included in the analysis target, by analyzing the obtained captured image, a length calculator configured to calculate a major axis length and a width of the perimeter stain, a time estimator configured to estimate a formation time of the perimeter stain by using the major axis length and the width of the perimeter stain, and an output controller configured to control the image of the perimeter stain and the formation time of the perimeter stain to be output through the output unit.

The length calculator may be further configured to generate a first guide line corresponding to a major axis of the perimeter stain, generate a second guide line corresponding to the width of the perimeter stain, and calculate the major axis length of the perimeter stain by using the first guide line, and calculate the width of the perimeter stain by using the second guide line.

The first guide line or the second guide line may be output through the output unit, and may be adjusted in location, size, or shape based on a user input.

The time estimator may be further configured to calculate the formation time of the perimeter stain by substituting the major axis length and the width of the perimeter stain in a pre-registered equation.

The electronic device may further include a first button used to obtain the captured image, and a second button used to calculate the formation time of the perimeter stain.

The electronic device may obtain a captured image from an external imaging device.

The electronic device may transmit the captured image and the formation time of the perimeter stain to an external device through the communication unit.

According to one or more embodiments, a computer program is recorded on a recording medium to execute a method of calculating a formation time of a perimeter stain.

According to one or more embodiments, other methods and other systems for implementing the present disclosure, and computer-readable recording media having recorded thereon computer programs for executing the methods are further provided.

Additional aspects, features, and advantages of the present disclosure will become apparent from the following detailed description, the accompanying drawings, and the appended claims.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

In this specification, a perimeter stain refers to a bloodstain formed when a drip stain is physically wiped. The perimeter stain may be formed from a drip stain due to a tussle between users, an intentional action for destruction of evidence, or the like. A formation time of the perimeter stain may serve as a critical clue to solving a crime. Unlike a spatter stain, the perimeter stain is formed when a bloodstain vertically fallen on a surface is wiped, and generally has a circular shape other than an elliptical shape. Since a bloodstain is dried from an edge thereof as time passes, the perimeter stain has a shape in which a center portion of the bloodstain, which is not yet dried, is removed. When a certain time has passed after a drip stain is formed, although a user physically wipes the drip stain, the perimeter stain may not be formed.

Figure 1:
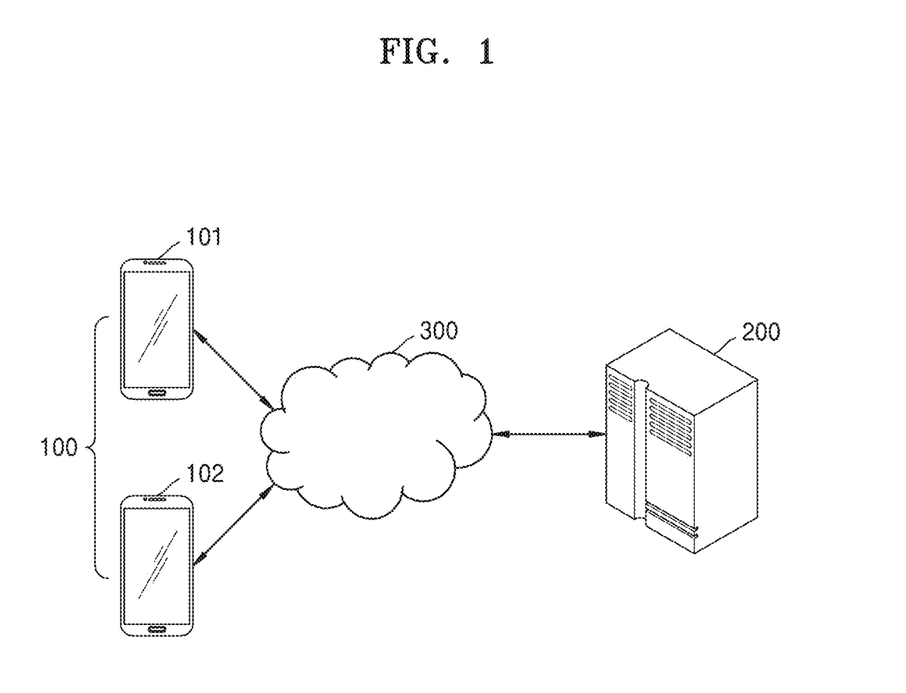
FIG. 1 is a schematic diagram of a bloodstain analysis system according to an embodiment of the present disclosure.

FIG. 1 is a schematic diagram of a bloodstain analysis system according to an embodiment of the present disclosure.

Referring to FIG. 1, the bloodstain analysis system according to an embodiment of the present disclosure includes a server 200, an electronic device 100, and a network 300 configured to connect the server 200 to the electronic device 100.

The bloodstain analysis system according to an embodiment of the present disclosure provides a service of calculating a formation time of a bloodstain. Specifically, the bloodstain analysis system provided according to an embodiment may upload data obtained by a user based on an experiment or a method of calculating a formation time of a bloodstain, which is described below, and share the uploaded data with other users. For example, the user may measure a major axis length and a width of a perimeter stain based on a formation time and upload data about the measured major axis length and the width. When the data is uploaded by the user, the bloodstain analysis system according to an embodiment registers the data in the server 200 and provides an interface configured to allow other users to check the data registered in the server 200. As such, the bloodstain analysis system according to an embodiment may build a database about the major axis length and/or the width of a perimeter stain based on a formation time.

The electronic device 100 refers to a communication device capable of using a web service in a wired or wireless communication environment and including a camera and a touchscreen. Herein, the electronic device 100 may be a portable device 101 or 102 of the user. Although FIG. 1 illustrates the portable device 101 or 102 as a smartphone, the scope of the present disclosure is not limited thereto, and any portable device including a camera and capable of installing therein an application programmed to execute a bloodstain analysis method provided according to an embodiment of the present disclosure may be used.

The electronic device 100 further includes an output unit configured to display a screen image and an input unit configured to receive data input from the user. The input unit may include, for example, a keyboard, a mouse, a trackball, a microphone, buttons, a touch panel, or the like, but is not limited thereto.

The network 300 connects the electronic device 100 to the server 200. For example, the network 300 provides an access route to the electronic device 100 to access and then transmit or receive packet data to or from the server 200.

Although not shown in FIG. 1, the server 200 according to an embodiment of the present disclosure may include memory, an input/output unit, a program storage, a controller, etc.

Figure 2:
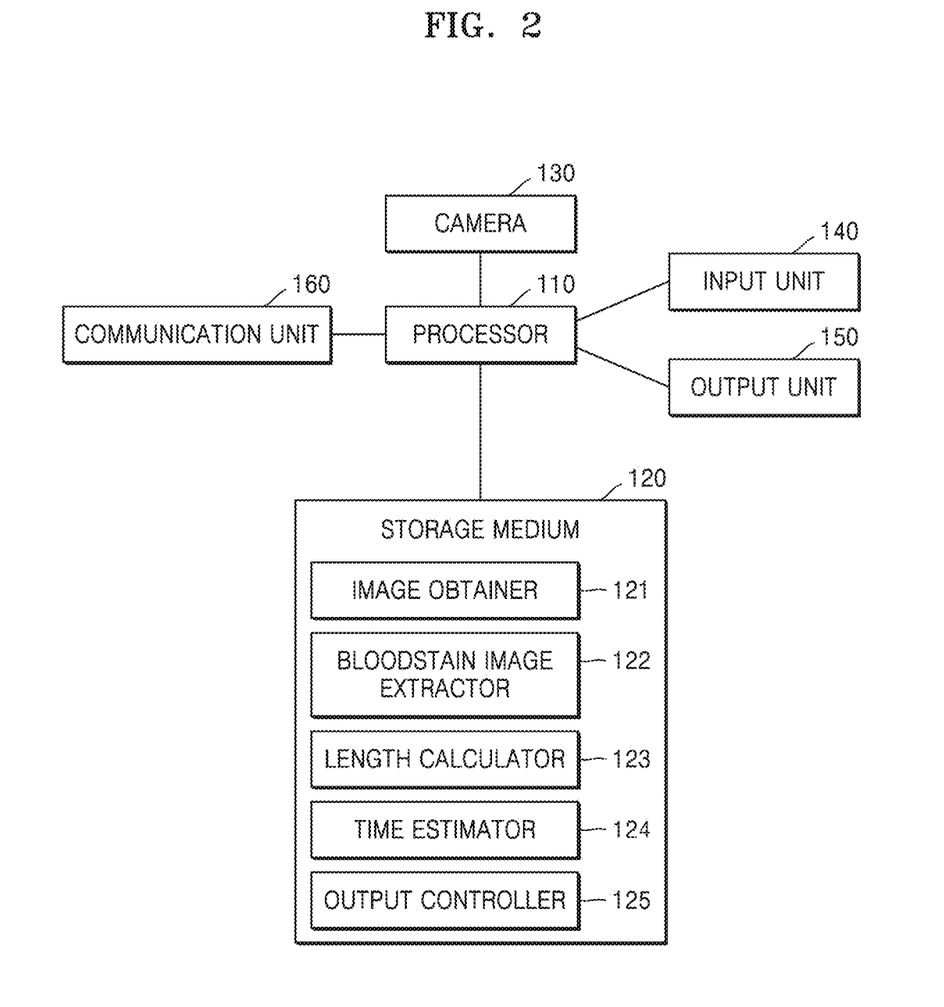
FIG. 2 is a block diagram of an electronic device for calculating a formation time of a perimeter stain, according to an embodiment of the present disclosure.

FIG. 2 is a block diagram of an electronic device 100 for calculating a formation time of a perimeter stain, according to an embodiment of the present disclosure.

As illustrated in FIG. 2, the electronic device 100 for calculating a formation time of a perimeter stain may include a processor 110, a storage medium 120, a camera 130, an input unit 140, an output unit 150, and a communication unit 160 to calculate a formation time of a perimeter stain by using a captured image of the perimeter stain.

At least one processor 110 may be provided. The processor 110 controls general operations of the electronic device 100. For example, the processor 110 may control the camera 130, the input unit 140, the output unit 150, and the communication unit 160 by executing programs stored in the storage medium 120.

The storage medium 120 may store programs for processing and controlling operations of the processor 110 and store input/output data.

The storage medium 120 may include at least one type of storage medium among flash memory, a hard disk, a multimedia card micro, card type memory (e.g., secure digital (SD) or extreme digital (XD) memory), random access memory (RAM), static random access memory (SRAM), read-only memory (ROM), electrically erasable programmable ROM (EEPROM), programmable ROM (PROM), magnetic memory, a magnetic disc, and an optical disc. Alternatively or additionally, the electronic device 100 may use a web storage or a cloud server serving as the storage medium 120 on the Internet.

The programs stored in the storage medium 120 may be classified into a plurality of modules based on functions thereof.

The camera 130 may obtain a still image or an image frame of a video in a capture mode by using an image sensor. The image captured by the image sensor may be processed using the module stored in the storage medium 120.

The image frame processed by the camera 130 may be stored in the storage medium 120 or be transmitted outside through the communication unit 160. Two or more cameras 130 may be provided depending on the configuration of the electronic device 100. The camera 130 may capture an image of an analysis target.

The input unit 140 refers to a means for inputting data by a user to control the electronic device 100. For example, the input unit 140 may include a keypad, a dome switch, a touchpad (e.g., a capacitive overlay type, a resistive overlay type, an infrared beam type, a surface acoustic wave type, an integral strain gauge type, or a piezoelectric type), a jog wheel, a jog switch, or the like, but is not limited thereto.

The output unit 150 outputs data processed by the electronic device 100. For example, the output unit 150 may output a captured image frame of a bloodstain. The output unit 150 may output user interfaces provided by executing the programs stored in the storage medium 120.

The communication unit 160 may include one or more elements configured to enable communication between the electronic device 100 and another external electronic device, a server, or the like.

The storage medium 120 may include an image obtainer 121, a bloodstain image extractor 122, a length calculator 123, a time estimator 124, and an output controller 125 to calculate a formation time of a perimeter stain.

The image obtainer 121 obtains the image captured by the camera 130. An analysis target may be a certain region of a crime scene including a perimeter stain. The image obtainer 121 may receive a captured image from an external electronic device.

The bloodstain image extractor 122 may extract an image of a perimeter stain by analyzing the obtained captured image. The bloodstain image extractor 122 may divide the captured image into images of a perimeter stain and a background and extract an image of a perimeter stain having characteristics of a perimeter stain.

The length calculator 123 calculates a major axis length and a width of the extracted perimeter stain. The length calculator 123 may calculate the longest diameter among one or more lines passing through the center of the perimeter stain, as the major axis length.

The length calculator 123 may calculate a width of a ring of the perimeter stain.

The length calculator 123 may generate a first guide line corresponding to a major axis of the perimeter stain and calculate the length of the first guide line as the major axis length of the perimeter stain. The location, length, color, and/or shape of the first guide line may be changed based on a user input. The location of the first guide line may be changed from a first point to a second point based on a drag input received through the input unit 140 and moving from the first point to the second point, and a diameter at the second point may be calculated as the major axis length of the perimeter stain.

The length calculator 123 may generate a second guide line corresponding to the width of a ring of the perimeter stain and set the length of the second guide line as the width of the perimeter stain. The location, length, color, and/or shape of the second guide line may be changed based on a user input.

The time estimator 124 estimates a formation time of the perimeter stain by using the major axis length and the width of the perimeter stain. Herein, the formation time of the perimeter stain refers to a difference in time between a timing at which a blood droplet initially falls and a timing at which the perimeter stain is formed due to a physical force.

The time estimator 124 may calculate the formation time of the perimeter stain in proportion to a trigonometric function value representing a ratio of the width to the major axis length.

The time estimator 124 may calculate the formation time of the perimeter stain by using the following equation.

$$t = k1 \sin(k2*s/d - k3)$$

Herein, t denotes the formation time of the perimeter stain (unit: minute), s denotes the width of the perimeter stain, d denotes the major axis length of the perimeter stain, and k1, k2, and k3 denote constants. In this time, k1, k2, and k3 may be changed based on a major axis length and a width of a perimeter stain based on a formation time, which are registered through a device.

Based on a test calculation, k1 may be a real number equal to or greater than 79 and equal to or less than 80, k2 may be a real number equal to or greater than 3.3 and equal to or less than 3.4, and k3 may be a real number equal to or greater than 0.04 and equal to or less than 0.05. In another embodiment, k1 may be 79.89, k2 may be 3.392, and k3 may be 0.4344.

The output controller 125 controls the estimated formation time of the perimeter stain to be output through the output unit 150. The output controller 125 may control the formation time of the perimeter stain to be output together with the image of the perimeter stain. The output controller 125 may control a screen image for providing the formation time of the perimeter stain, to be output through an external electronic device.

The formation time estimated according to the current embodiment may be stored in a database together with the image of the perimeter stain, the major axis length, and the width.

As such, a situation that happened at a crime scene may be deduced using the estimated formation time, and a clue to solving a crime may be found using the deduced situation.

Figure 3:
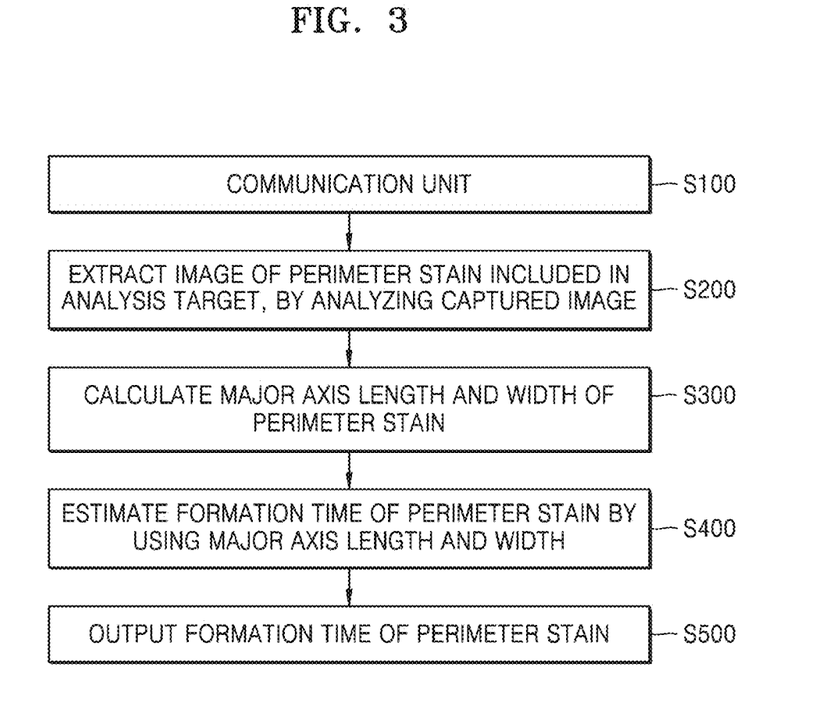
FIG. 3 is a flowchart of a method of calculating a formation time of a perimeter stain, according to an embodiment of the present disclosure.

FIG. 3 is a flowchart of a method of calculating a formation time of a perimeter stain, according to an embodiment of the present disclosure.

Referring to FIG. 3, initially, the electronic device 100 for calculating a formation time of a perimeter stain obtains a captured image of an analysis target (S100). In this case, the captured image may be an image of a crime scene which is directly captured by the camera 130, or a previously captured image stored in a storage medium. Alternatively, the captured image may be downloaded and obtained from another electronic device 100 or the server 200 of the bloodstain analysis system.

When an image of a crime scene is directly captured by the camera 130, a user may obtain the captured image by touching a capture button C1 displayed on a screen image A1.

After the captured image is obtained, an image of a perimeter stain included in the analysis target is extracted by analyzing the obtained captured image (S200). Herein, the analysis target may be a certain region where perimeter stains are distributed at the crime scene. The captured image may be divided into images of a plurality of bloodstains and a background. The bloodstain image extractor 122 may divide the captured image into unit regions and define the unit regions as images of a background and a plurality of bloodstains by using the difference between color values or gray scales thereof. Among the plurality of bloodstains included in the captured image, the bloodstain image extractor 122 extracts an image of a perimeter stain having characteristics of a perimeter stain.

The electronic device 100 calculates a major axis length d and a width s of the perimeter stain (300). The perimeter stain B is formed when a drip stain fallen from a blood source on a surface such as a wall or a floor is pressed or wiped by a person. Since an edge of the drip stain, which is dried fast, remains and a center portion of the drip stain, which is not yet dried, is removed, the perimeter stain B has a ring shape. Unlike a spatter stain having an acute angle of impact to a surface, the perimeter stain B is formed from a bloodstain perpendicularly fallen on a surface.

Figure 5A:
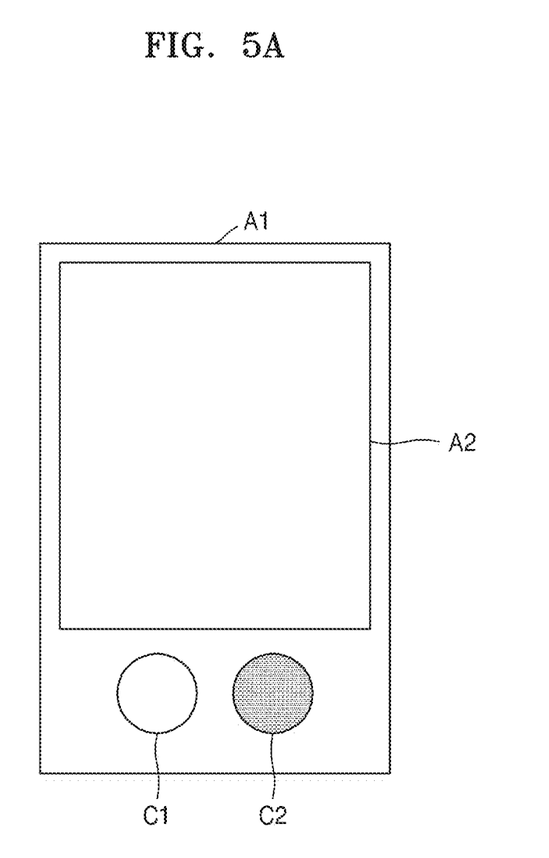
FIGS. 5A to 5F are images of examples of user interfaces provided by the electronic device.
Figure 5B:
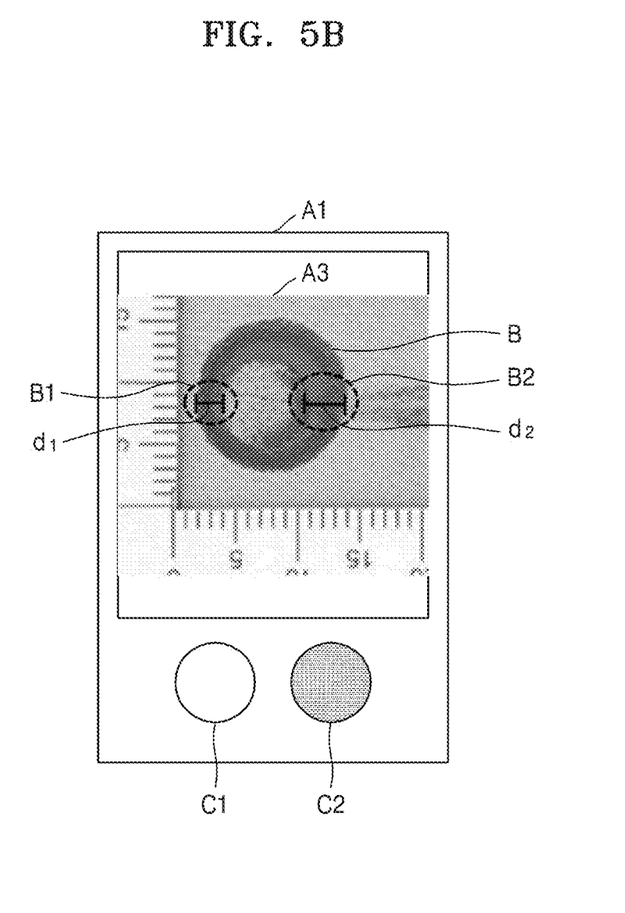
Figure 5C:
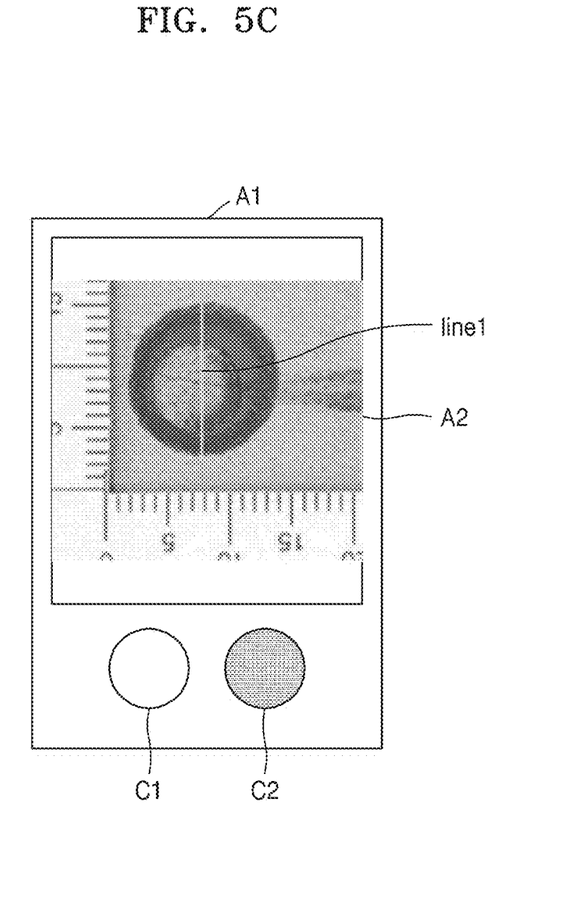
Figure 5D:
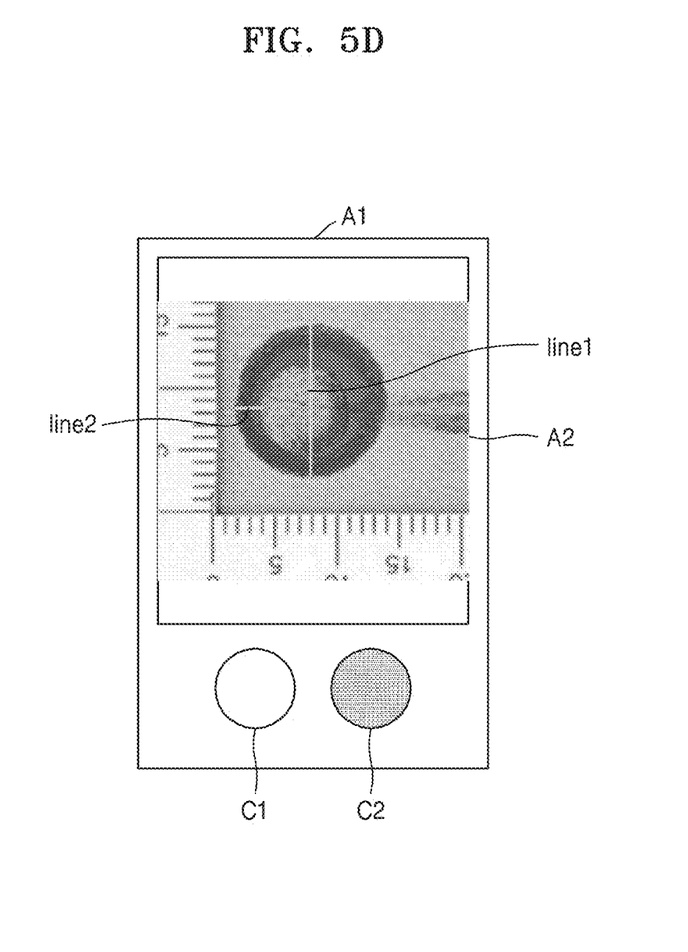
Figure 5E:
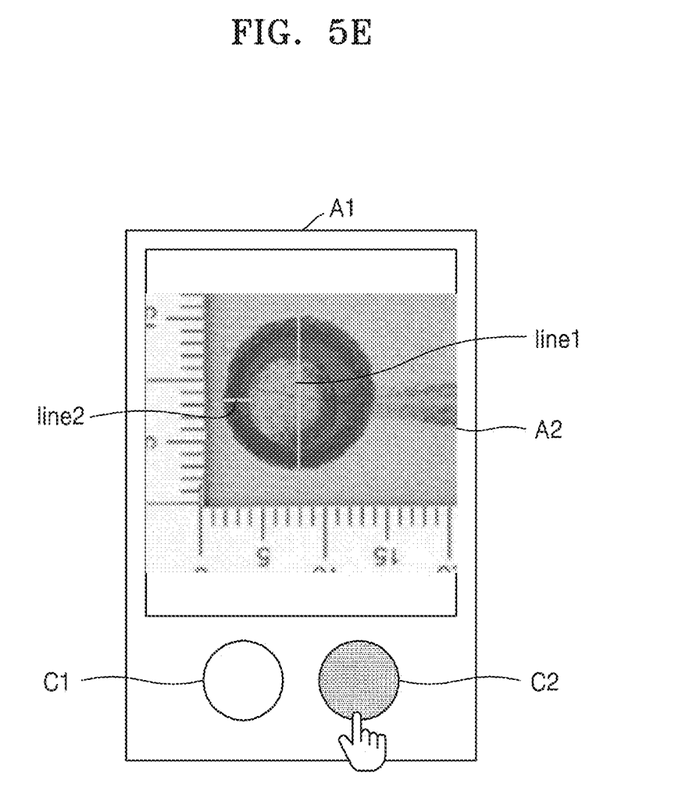

In this case, the width s is a width near a start point of a force applied to the perimeter stain. In FIG. 5B, the width of the perimeter stain B varies from d1 to d2. It may be inferred that a force is applied in a direction from a portion B1 where the perimeter stain B has the smallest width toward a portion B2 where the perimeter stain B has the largest width. In this case, the width d1 of the portion B1 near a start point of the applied force is set as the width of the perimeter stain B.

The electronic device 100 estimates a formation time of the perimeter stain by substituting the major axis length and the width of the perimeter stain in a pre-registered equation (S400). The major axis length of the perimeter stain may be replaced by a diameter. Since the perimeter stain is close to a circular shape, the major axis length may be replaced by a diameter.

Figure 5F:
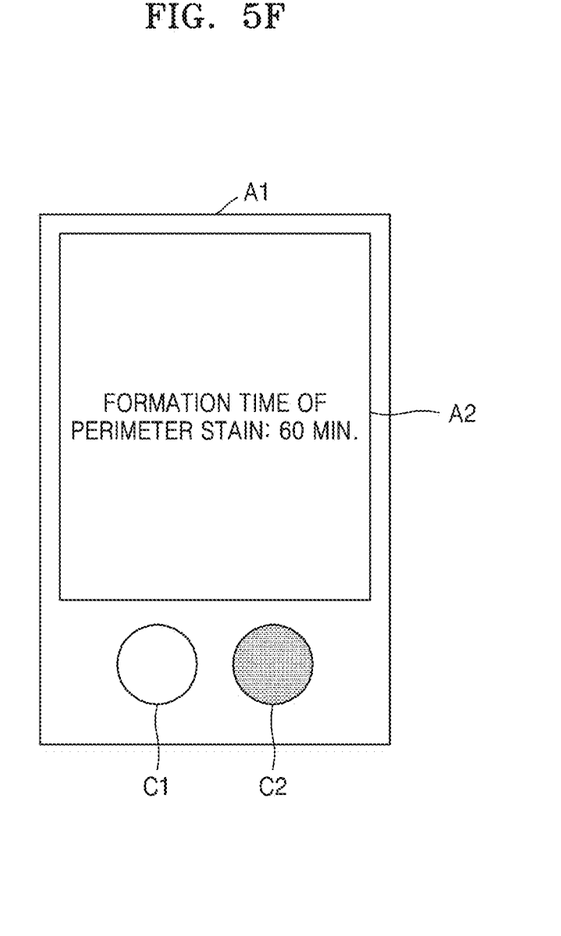

As illustrated in FIG. 5F, the electronic device 100 provides a screen image A4 for outputting the estimated formation time of the perimeter stain (S500). The screen image A4 including the formation time of the perimeter stain may be output through the output unit 150 of the electronic device 100, or through an output unit of another device.

Figure 4:
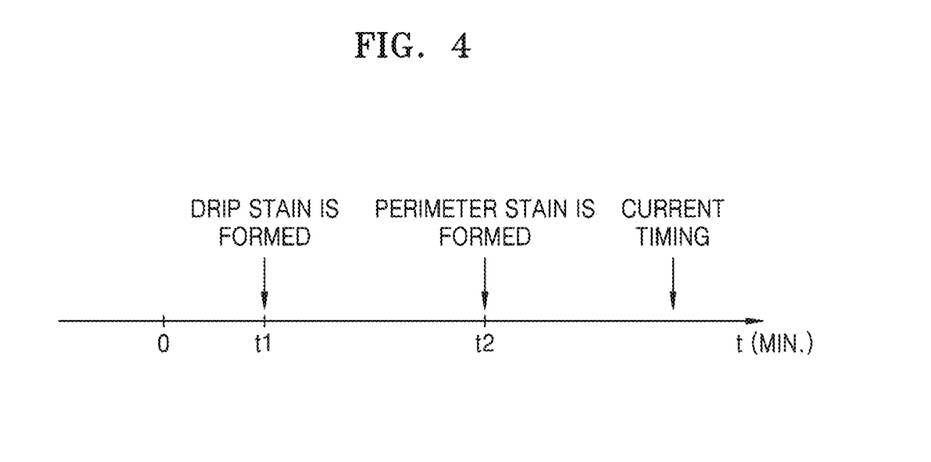
FIG. 4 is a timing diagram for describing the concept of a formation time of a perimeter stain.

As illustrated in FIG. 4, a formation time t2−t1 of a perimeter stain, which is estimated by the electronic device 100 according to an embodiment of the present disclosure, refers to a period of time between a timing t1 at which a drip stain is formed and a timing t2 at which the perimeter stain is formed from the drip strain. In general, the formation time of the perimeter stain is estimated by using the electronic device 100 according to the current embodiment at an arbitrary timing after the perimeter stain is formed.

FIGS. 5A to 5F are images of examples of user interfaces provided by the electronic device 100.

According to embodiments of the present disclosure, when an installed program is executed, the electronic device 100 provides a screen image A1 including a preview image A2 showing a currently sensed image frame, a capture button C1, and a calculate button C2 through the output unit 150.

A current image frame A3 is captured when a user touches the capture button C1, and calculation of a formation time of a perimeter stain B included in the captured image A3 is started when the user touches the calculate button C2. When a certain time has passed after the calculate button C2 is touched, the formation time of the perimeter stain is output.

After the capture button C1 is touched, the electronic device 100 may generate a first guide line corresponding to a major axis of the perimeter stain and a second guide line corresponding to a width of the perimeter stain, and overlay the first and second guide lines on the captured image A3. The user may change the location of the first guide line or the second guide line before touching the calculate button C2, and the first guide line corresponding to the major axis of the perimeter stain or the second guide line corresponding to the width of the perimeter stain may be displayed on the changed location.

After the calculate button C2 is touched, the electronic device 100 may calculate a major axis length and a width of the perimeter stain and estimate a formation time of the perimeter stain by using the major axis length and the width of the perimeter stain. The electronic device 100 may set an equation based on stored data about the major axis length and the width of the perimeter stain based on the formation time. The electronic device 100 may estimate the formation time of the perimeter stain by substituting the major axis length and the width of the perimeter stain in the equation. The electronic device 100 may provide an output screen image A4 including the formation time of the perimeter stain. In this case, the electronic device 100 may be implemented to output the output screen image A4 through an output unit of another electronic device connected through a communication network.

In another embodiment, the formation time of the perimeter stain may be determined by applying a different equation depending on the type of a surface on which the perimeter stain is located (e.g., wallpaper, a tile, or paper). In actual cases, since a time taken until a bloodstain is dried may vary depending on the type of the surface, a different equation may be applied depending on the type of the surface. Even when perimeter stains have the same shape, a time taken until a perimeter stain located on wallpaper is dried differs from a time taken until a perimeter stain located on a tile is dried.

A formation time of a perimeter stain, which serves as a critical clue to deducing an action at a crime scene, may be rapidly calculated based on an electronic device for calculating a formation time of a perimeter stain, a method of calculating a formation time of a perimeter stain, and a computer program recorded on a recording medium to execute the method, according to embodiments of the present disclosure.

The device described above may be implemented by hardware components, software components, and/or a combination thereof. For example, the device and components described in the embodiments may be implemented using one or more general-purpose or special-purpose computers, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and one or more software applications running on the OS. In addition, the processing device may access, store, manipulate, process, and generate data in response to execution of the software. For ease of understanding, the processing device has been described as a single device. However, one of ordinary skill in the art will understand that the processing device may include multiple processing elements and/or multiple types of processing elements. For example, the processing device may include multiple processors or a processor and a controller. Other processing configurations, such as parallel processors, are also possible.

The software may include computer programs, code, instructions, or a combination thereof and may configure the processing device to operate as desired or instruct the processing device independently or collectively. In order to be interpreted by the processing device or to provide instructions or data to the processing device, the software and/or data may be embodied permanently or temporarily in any type of a machine, a component, a physical device, virtual equipment, a computer storage medium or device, or a transmission signal wave. The software may be distributed over a network-coupled computer system and stored or executed in a distributed fashion. The software and data may be stored in one or more computer-readable recording media.

The method according to the embodiments may be implemented in the form of program instructions that can be executed through various computer means, and may be recorded in a computer-readable recording medium. The computer-readable recording medium can store program instructions, data files, data structures, or combinations thereof. The program instructions recorded in the computer-readable recording medium may be those specially designed and constructed for the purposes of the embodiments, or they may be of the kind well known and available to one of ordinary skill in the art of computer software. Examples of the computer-readable recording media include magnetic media (e.g., hard disks, floppy disks, and magnetic tapes), optical media (e.g., CD-ROMs or DVDs), magneto-optical media (e.g., floptical disks), and hardware devices (e.g., ROMs, RAMs, or flash memories, etc.) that are specially configured to store and execute program instructions. Examples of the program instructions include both machine code, such as produced by a compiler, and high-level language code that may be executed by the computer using an interpreter. The hardware devices may be configured to operate as one or more software modules to perform operations of the embodiments, and vice versa.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of estimating a formation time of a perimeter stain; the method performed by at least one processor of an electronic device and comprising:
    obtaining a captured image of an analysis target by using a camera;
    extracting an image of a perimeter stain comprised in the analysis target, by analyzing the obtained captured image;
    calculating a major axis length and a width of the perimeter stain;
    estimating a formation time of the perimeter stain by using the major axis length and the width of the perimeter stain; and
    outputting the image of the perimeter stain and the estimated formation time of the perimeter stain.

2. The method of claim 1, wherein the calculating of the major axis length and the width of the perimeter stain comprises:
    generating a first guide line corresponding to a major axis of the perimeter stain;
    generating a second guide line corresponding to the width of the perimeter stain; and
    calculating the major axis length of the perimeter stain by using the first guide line, and calculating the width of the perimeter stain by using the second guide line.

3. The method of claim 2, wherein at least one of the first guide line or the second guide line is output through an output unit and adjusted in location, size, or shape based on a user input.

4. The method of claim 1, wherein the estimating of the formation time of the perimeter stain comprises estimating the formation time of the perimeter stain by substituting the major axis length and the width of the perimeter stain in a pre-registered equation.

5. The method of claim 1, wherein the electronic device comprises a first button used to obtain the captured image and a second button used to estimate the formation time of the perimeter stain.

6. The method of claim 1, wherein the obtaining of the captured image of the analysis target comprises obtaining a captured image from an external imaging device.

7. The method of claim 1, further comprising transmitting the captured image and the estimated formation time of the perimeter stain to an external device, after the estimated formation time of the perimeter stain is estimated.

8. The method of claim 1, wherein estimating the formation time of the perimeter stain comprises determining a trigonometric function value whose argument includes a ratio of the width of the perimeter stain to the major axis length.

9. The method of claim 8, wherein:
    the trigonometric function is sine; and
    the argument is a first value minus a second value, the first value being the ratio of the width of the perimeter stain to the major axis length multiplied by a first constant, the second value being a second constant.

10. The method of claim 9, wherein estimating the formation time of the perimeter stain further comprises multiplying the trigonometric function value by a third constant.

11. The method of claim 1, further comprising varying a formula used in estimating the formation time of the perimeter stain dependent on a type of a surface on which the perimeter stain is located.

12. The method of claim 1, wherein:
    the perimeter stain is a ring having unequal width around a circumference of the ring, and
    the method further comprises determining a direction of a force applied to form the perimeter stain as a direction from a portion of the ring having a smallest width to a portion of the ring having a largest width.

13. The method of claim 12, further comprising using the smallest width in estimating the formation time of the perimeter stain.

14. The method of claim 1, wherein the estimated formation time of the perimeter stain represents an estimated difference in time between a time when blood is introduced to a surface and a time when the perimeter stain is formed due to application of physical force to the blood.

15. An electronic device comprising a camera, an input unit, an output unit, a processor, and a storage medium having stored therein instructions executable by the processor,
    wherein the processor is configured to:
        obtain a captured image of an analysis target by using the camera;
        extract an image of a perimeter stain comprised in the analysis target, by analyzing the obtained captured image;
        calculate a major axis length and a width of the perimeter stain;

estimate a formation time of the perimeter stain by using the major axis length and the width of the perimeter stain; and output the image of the perimeter stain and the estimated formation time of the perimeter stain through the output unit.

16. The electronic device of claim 15, wherein the processor is further configured to:

generate a first guide line corresponding to a major axis of the perimeter stain;

generate a second guide line corresponding to the width of the perimeter stain; and calculate the major axis length of the perimeter stain by using the first guide line, and calculate the width of the perimeter stain by using the second guide line.

17. The electronic device of claim 16, wherein at least one of the first guide line or the second guide line is output through the output unit, and is adjusted in location, size, or shape based on a user input.

18. The electronic device of claim 17, wherein the processor is further configured to estimate the formation time of the perimeter stain by substituting the major axis length and the width of the perimeter stain in a pre-registered equation.

19. The electronic device of claim 15, further comprising a first button used to obtain the captured image, and a second button used to estimate the formation time of the perimeter stain.

20. The electronic device of claim 19, wherein the electronic device is configured to obtain a captured image from an external imaging device, and to estimate a formation time of a perimeter stain comprised in the captured image.

21. The electronic device of claim 19, wherein the electronic device transmits the captured image and the estimated formation time of the perimeter stain to an external device through the communication unit.

* * * * *

UNITED STATES PATENT AND TRADEMARK OFFICE
CERTIFICATE OF CORRECTION

PATENT NO. : 10,782,283 B2  
APPLICATION NO. : 16/175646  
DATED : September 22, 2020  
INVENTOR(S) : Park et al.

Page 1 of 1

It is certified that error appears in the above-identified patent and that said Letters Patent is hereby corrected as shown below:

In the Claims

In Column 9, Line 44, in Claim 1, delete "stain;" and insert --stain,-- therefor Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*